US010545116B2

United States Patent
Lu et al.

(10) Patent No.: US 10,545,116 B2
(45) Date of Patent: Jan. 28, 2020

(54) NANO DIPOLE SENSORS

(71) Applicant: International Business Machines Corporation, Armonk, NY (US)

(72) Inventors: Minhua Lu, Mohegan Lake, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 15/826,383

(22) Filed: Nov. 29, 2017

(65) Prior Publication Data

US 2019/0162695 A1    May 30, 2019

(51) Int. Cl.
*G01N 27/416*    (2006.01)
*H01L 29/73*    (2006.01)
*G01N 27/414*    (2006.01)

(52) U.S. Cl.
CPC ............ *G01N 27/416* (2013.01); *H01L 29/73* (2013.01); *G01N 27/4141* (2013.01); *G01N 27/4145* (2013.01)

(58) Field of Classification Search
CPC ...... H01L 29/73; G01N 27/49; G01N 27/416; G01R 19/15
See application file for complete search history.

(56) References Cited

U.S. PATENT DOCUMENTS

| 5,486,481 A * | 1/1996 | Sundaram | H01L 29/735 |
| | | | 148/DIG. 96 |
| 7,960,753 B2 * | 6/2011 | Conway | B82Y 20/00 |
| | | | 257/104 |
| 2006/0263255 A1 * | 11/2006 | Han | B82Y 10/00 |
| | | | 422/83 |
| 2016/0169834 A1 * | 6/2016 | Ning | G01N 27/4145 |
| | | | 205/792 |
| 2016/0290955 A1 | 10/2016 | Zhong et al. | |
| 2016/0290957 A1 * | 10/2016 | Ram | A61B 5/1477 |
| 2018/0334697 A1 * | 11/2018 | Shachar | C12Q 1/6825 |

OTHER PUBLICATIONS

C. Hu, Modern Semiconductor Devices for Integrated Circuits, Chapter 8, Bipolar Transistor, 2009, p. 291-323. (Year: 2009).*
Sufi Zafar et al., "A comparison between bipolar transistor and nanowire field effect transistor biosensors," Applied Physics Letters 106, 063701 (2015); doi: 10.1063/1.4907611, accepted Jan. 25, 2015; published online Feb. 12, 2015, Cover Plus pp. 063701-1 to 063701-4.
Girish S. Kulkarni et al., "Nanoelectronic Heterodyne Sensor: A New Electronic Sensing Paradigm," Accounts of Chemical Research special issue "Nanoelectrochemistry," pp. 1-9.
(Continued)

*Primary Examiner* — Luan V Van
*Assistant Examiner* — Caitlyn Mingyun Sun
(74) *Attorney, Agent, or Firm* — L. Jeffrey Kelly; Otterstedt, Wallace & Kammer, LLP (57) ABSTRACT

A bipolar junction transistor is provided; the transistor has an emitter, a base, and a collector. The base is coupled to a sensing electrode. The sensing electrode is immersed in a fluid to be analyzed. The bipolar junction transistor is biased into the active region. An AC excitation of one of the emitter and the base is caused. A measurement is carried out on a collector current resulting from the AC excitation, to analyze the fluid.

13 Claims, 9 Drawing Sheets

(56) References Cited

OTHER PUBLICATIONS

Wikipedia, Debye length, Downloaded Oct. 25, 2017 From https://en.wikipedia.org/wiki/Debye_length, pp. 1-6.
Wikipedia, Double layer (surface science), Downloaded Oct. 24, 2017 From https://en.wikipedia.org/wiki/Double_layer_(surface_science), pp. 1-8.
Wikipedia, Lock-in amplifier, Downloaded Oct. 21, 2017 From https://en.wikipedia.org/wiki/Lock-in_amplifier, pp. 1-5.

* cited by examiner

NANO DIPOLE SENSORS

BACKGROUND

The present invention relates to the electrical and electronic arts, and more specifically, to bio sensor devices and the like.

Current bio sensing techniques typically employ direct current (DC) charge sensing. While this type of sensing has proven quite useful, it nevertheless has certain limitations. DC sensing is unable to sense neutral molecules. Furthermore, the Debye length limits charge detectability in high ionic concentration solutions. In addition, in some instances, the charge might form a double layer near the electrodes, modify the surface potential of the electrodes, and result in drifting in measurement. Even further, in DC sensing, a galvanic reaction can have an impact on electrode lifetime and/or biological tissues.

SUMMARY

Embodiments of the present disclosure provide circuitry for Nano dipole sensors and related sensors, circuits, and/or techniques. According to an embodiment of the present invention, an exemplary method includes providing a bipolar junction transistor having an emitter, a base, and a collector, said base being coupled to a sensing electrode; immersing said sensing electrode in a fluid to be analyzed; biasing said bipolar junction transistor into the active region; causing an AC excitation of one of said emitter and said base; and carrying out a measurement on a collector current resulting from said AC excitation, to analyze said fluid.

According to another embodiment of the present invention, another exemplary method includes providing a transistor having at least three terminals, at least one of said three terminals being coupled to a sensing electrode; immersing said sensing electrode in a fluid to be analyzed; biasing said transistor into an operating region suitable for sensing; causing an AC excitation on at least one of said three terminals; and carrying out a measurement on a current resulting from said AC excitation, to analyze said fluid. Said step of causing said AC excitation to said at least one of said three terminals comprises at least one of: surface plasmon coupling electromagnetic waves to said at least one of said three terminals via at least one of a prism, a waveguide, and a grating; and impinging acoustic waves on a piezoelectric material coupled to said at least one of said three terminals.

According to a further embodiment of the present invention, an exemplary apparatus for analyzing a fluid includes a sensing electrode; a bipolar junction transistor having an emitter, a base, and a collector, said base being coupled to said sensing electrode; a vessel configured to contain said sensing electrode and the fluid to be analyzed; a biasing circuit configured to bias said bipolar junction transistor into the active region; an AC source configured to cause AC excitation of one of said emitter and said base; and a measurement circuit having: a first input coupled to said collector such that a collector current resulting from said AC excitation comprises a first input to said measurement circuit; and an output from which at least one frequency component can be extracted.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

Techniques of the present invention can provide substantial beneficial technical effects. For example, one or more embodiments provide one or more of:

overcoming charge trapping found in DC approaches;
increased measurement speed;
detection of electrically neutral molecules;
in certain circumstances, provision of information about molecular orientation (depending on the product of the dipole and the field).

These and other features and advantages of the present invention will become apparent from the following detailed description of illustrative embodiments thereof, which is to be read in connection with the accompanying drawings.

DETAILED DESCRIPTION

As noted, current bio sensing techniques typically employ direct current (DC) charge sensing. While this type of sensing has proven quite useful, it nevertheless has certain limitations. DC sensing is unable to sense neutral molecules. Furthermore, the Debye length limits charge detectability in high ionic concentration solutions. In addition, in some instances, the charge might form a double layer near the electrodes, modify the surface potential of the electrodes, and result in drifting in measurement. Even further, in DC sensing, a galvanic reaction can have an impact on electrode lifetime and/or biological tissues. Galvanic reaction problems are more likely when the DC voltage is large.

Figure 1:
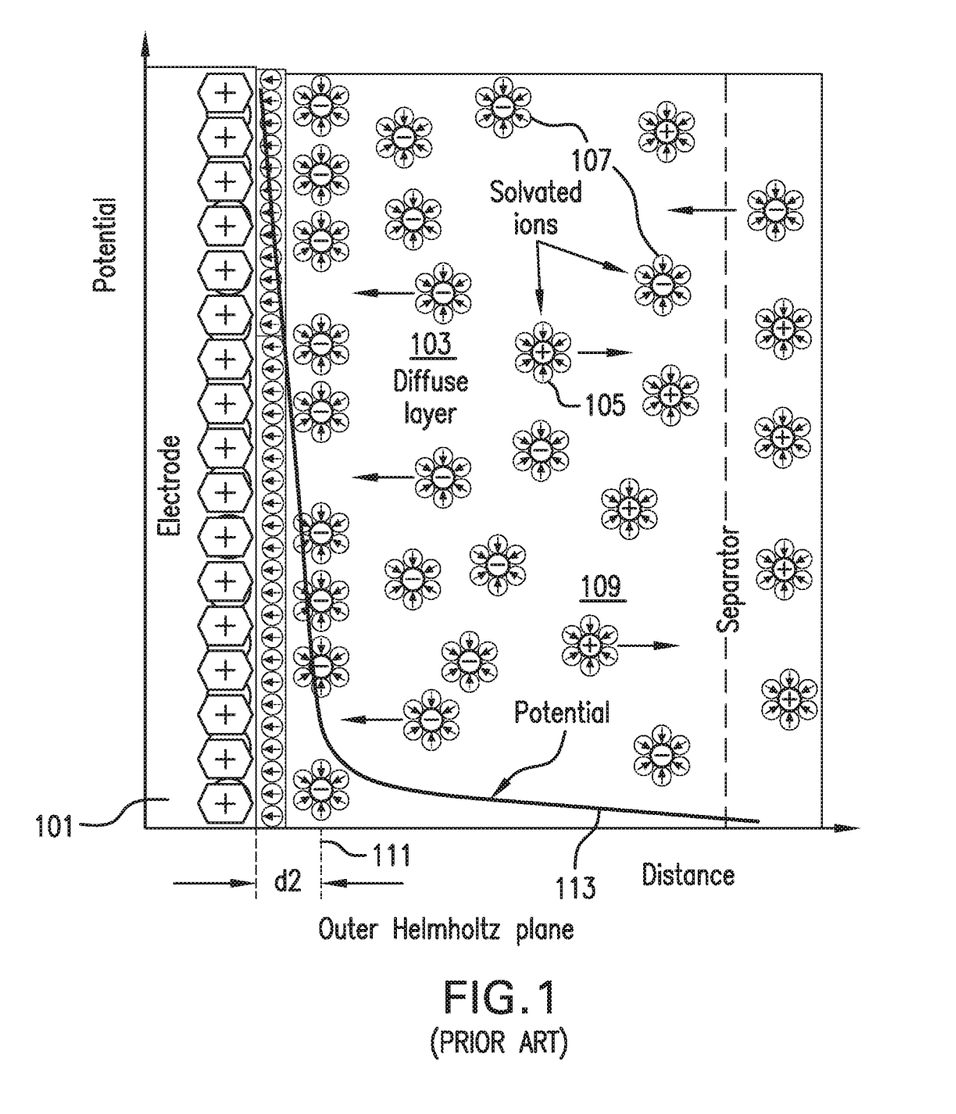
FIG. 1 depicts formation of a double layer in a prior art DC technique.

Thus, in prior art DC techniques, an electrical double layer forms on a surface exposed to fluid. The charged double layer has great influence on the electrochemical behavior of the electrodes. For DC charge sensing, the surface charges that accumulate on the electrodes can alter the electrical potential near the electrodes and screen the charge form the liquid. Referring to FIG. 1, a double layer is a structure that appears on an object's surface when it is exposed to a fluid. The object here is the electrode 101. The double layer refers to two parallel layers of charge surrounding the object: (i) the surface charge (either positive or negative), includes ions adsorbed onto the object due to chemical interactions; and (ii) ions attracted to the surface charge via the Coulomb force, electrically screening the first layer. This second layer is loosely associated with the object and is made of free ions (105 positive, 107 negative) that move in the fluid 109 under the influence of electric attraction and thermal motion rather than being firmly anchored. It is thus called the "diffuse layer" 103. More specifically, FIG. 1 shows an electronic conductor 101 brought in contact with a solid or liquid ionic conductor (electrolyte 109), wherein a common boundary (interface) among the two phases appears (outer Helmholtz plane 111 at d2). The charged electrode 101 (positive charge) immersed in electrolytic solution 109 repels the co-ions 105 of the charge while attracting counter ions 107 to its surface. Two layers of opposite polarity charges thus form at the interface between electrode 101 and electrolyte 109. Curve 113 shows the electric potential (vertical axis) plotted against distance from the electrode (horizontal axis); the "separator" line shows the location where the potential approaches zero. The accumulation of oppositely charged particles (here, negative) screens the electrode and alters the potential.

One or more embodiments advantageously provide AC modulated sensing with a BJT. Note that use of AC modulation of appropriate frequency (see discussion below about frequency selection) can break some of the charge trapping and adverse DC field effects on the system; the charge diffusion process is fundamentally slow. The second order product of the AC modulation is related to the dipole and induced dipole oscillation by the AC field, which is independent of the absolute charge. The dipole oscillation can follow the driving field, resulting in fast measurement. The dipoles and induced dipole exists in electrically neutral molecules, which charge sensing cannot detect. Furthermore, dipole sensing can provide information about molecular orientation. Use of AC modulation therefore advantageously facilitates sensing in high ionic solutions, and/or of electrically neutral molecules.

Regarding frequency selection, ionic charge diffusion in aqueous solution is complex. It depends on the number of the charge, the shape and size of the charged species, viscosity of the solution, ionic strength of the solution, and interaction with other species in the solution. Typically, it is a slow process, which can range from $10^{-6}$ to 1 sec. Thus, the AC frequency can be from $10^1$-$10^6$ or even $10^1$-$10^9$ Hz. Given the teachings herein, the skilled artisan will be enabled to design straightforward experiments and/or use known simulation techniques to determine the appropriate frequency for a given application.

One or more embodiments provide a BJT-based electrochemical sensor. FETs and BJTs are capable of charge sensing using conventional techniques, but cannot sense dipoles. Compared to FETs, BJTs are smaller, higher sensitivity, higher accuracy, lower current, and have demonstrated good charge sensing, e.g., Cl⁻ (chloride concentration) and pH (potential of hydrogen, used to specify the acidity or basicity of an aqueous solution), and the like.

Note that both discrete and integrated BJTs can be used in one or more embodiments. In one or more embodiments, BJTs operate as transducers, in the active region.

Figure 2:
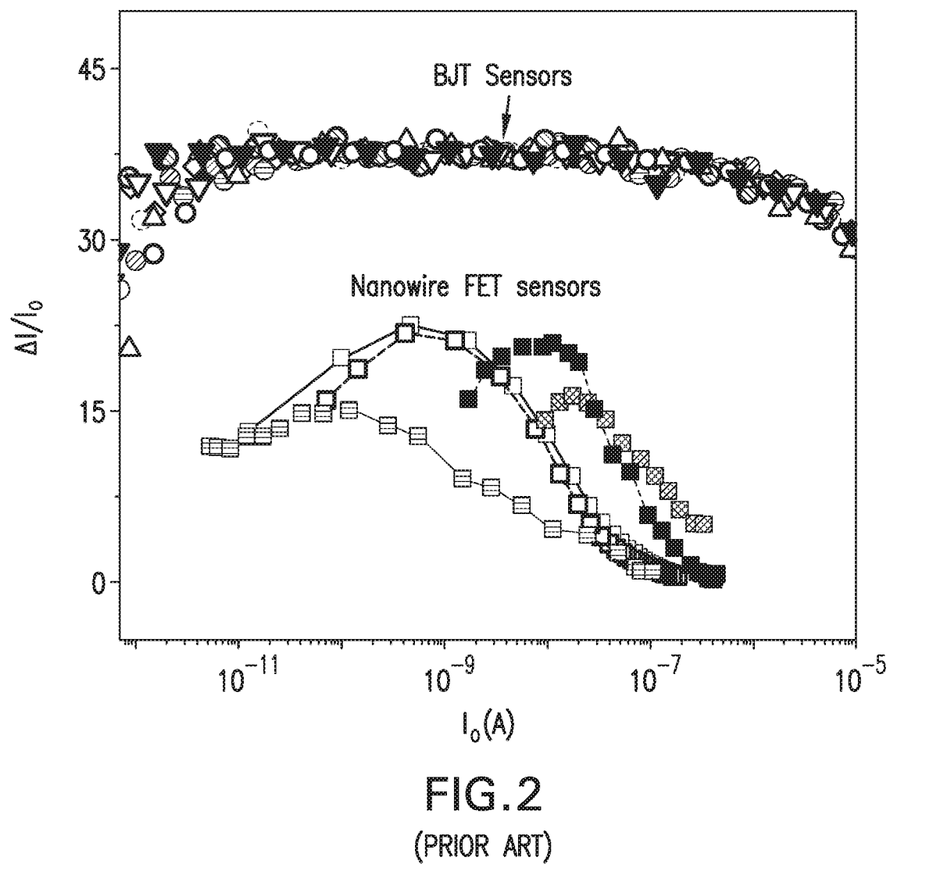
FIG. 2 compares bipolar junction transistor (BJT) sensors with nanowire Field-effect transistor (FET) sensors, as is known from the prior art.

FIG. 2 shows a sensitivity comparison between bipolar transistors and nanowire FET biosensors. Data for two types of bipolar transistors are shown: open symbols denote heterojunction bipolar transistor (HBT) sensors (with SiGe base) and solid lines denote BJT sensors (with silicon base) data. $I_C$ is the sensing current for bipolar transistor sensors whereas $I_d$ is the sensing current for FET sensors. Sensitivity is defined as the relative change in the sensing signal, $\Delta I_c/I_c$, corresponding to a unit change in the surface potential. Reference is made to Sufi Zafar, Marwan Khater, Vibhor Jain, and Tak Ning, "A comparison between bipolar transistor and nanowire field effect transistor biosensors," Applied Physics Letters 106, 063701 (2015); doi: 10.1063/1.4907611, expressly incorporated herein by reference in its entirety for all purposes.

One or more embodiments can employ a variety of AC modulation methods. Current modulation is employed in one or more embodiments. In addition to AC current modulation, electromagnetic waves, such RF, mm wave and infrared, and optical waves, can be used to modulate the surface state of the electrodes by surface plasmon coupling through a coupling medium such as a prism, waveguide, or grating. Acoustic waves can also be employed in one or more embodiments, via piezoelectric coupling. These electromagnetic, optical, and/or acoustic techniques introduce high frequency modulation directly on the electrode. Non-limiting examples of appropriate metals for use include Au, Al, and Ag. Acoustic waves can also be used for AC modulation through piezoelectric coupling. For BJTs, the AC modulation can be applied to either the emitter or the base.

For the avoidance of doubt, AC current modulation is known for use in connection with FETs. One or more embodiments instead employ AC current modulation with BJTs. Furthermore, use of electromagnetic, optical, and/or acoustic techniques to introduce high frequency modulation directly on the electrode has not been employed heretofore with either BJTs or FETs, but is advantageously provided, in one or more embodiments, for use with either type of transistor.

In prior-art techniques using FETs, the AC modulation is typically applied to the source. On or more embodiments instead employ BJTs with AC modulation applied to the emitter or base.

Figure 3:
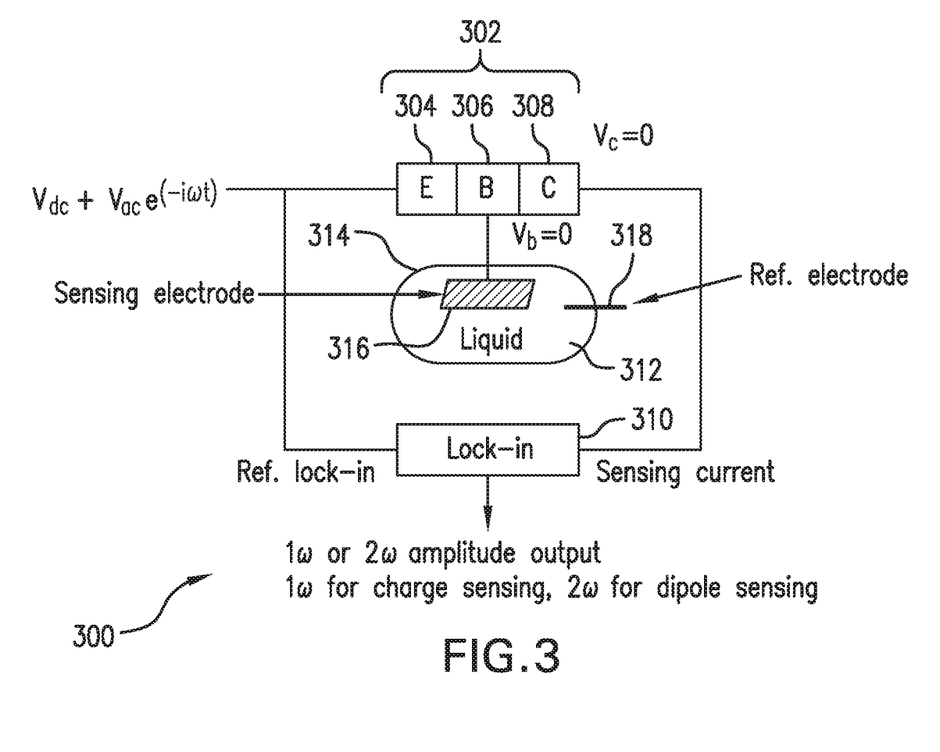
FIG. 3 depicts a sensor employing a BJT with AC modulation at the emitter, according to an aspect of the invention.

Referring to FIG. 3, an exemplary sensor structure 300 is provided for a current modulation solution. A BJT 302 includes an emitter E 304, a base B 306, and a collector C 308. The BJT is combined with a lock-in amplifier 310 for AC modulation used for sensing applications in a liquid solution 312. For AC modulation, the current, I, is given by:

$$I = (G_{dc} + G_{ac}e^{(-i\omega t)})(V_{dc} + V_{ac}e^{(-i\omega t)}) = G_{dc}V_{dc} + G_{dc}V_{ac}e^{(-i\omega t)} + G_{ac}V_{dc}e^{(-i\omega t)}) + G_{ac}V_{ac}e^{(-i2\omega t)} \quad (1)$$

Note that if $V_{dc}=0$, $I=G_{dc}V_{ac}e^{(-i\omega t)}) + G_{ac}V_{ac}e^{(-i\omega t)}$. (2)

The $G_{dc}$ and $G_{ac}$ parameters are the transconductances for direct and alternating current, respectively; iω is the complex frequency. The skilled artisan will know how to determine the transconductance for configurations of interest.

The liquid solution 312 is contained in a suitable test vessel 314. The sensing electrode 316 is immersed in the liquid 312 and coupled to the base B 306. Note also the reference electrode 318, which is maintained at 0 volts (grounded). The DC and AC components of the input signal, $V_{dc}+V_{ac}e^{(-i\omega t)}$, are applied to the emitter E 304. The base and collector are maintained at ground potential. The input signal $V_{dc}$ $V_{ac}e^{(-i\omega t)}$ also is coupled to the lock-in amplifier 310 as the reference signal. The sensing current (i.e. collector current) I is the other input to the lock-in amp 310. As indicated by the notation "1f or 2f amplitude output," the first frequency component can be taken at the output for charge sensing applications, and the second frequency component for dipole sensing applications. The skilled artisan will be able to extract the desired frequencies using Fourier analysis or other appropriate techniques.

Note that both npn and pnp BJTs can be employed, as appropriate, in one or more embodiments. Both nFETs and pFETs can be employed, as appropriate, in FET-based embodiments.

Figure 4:
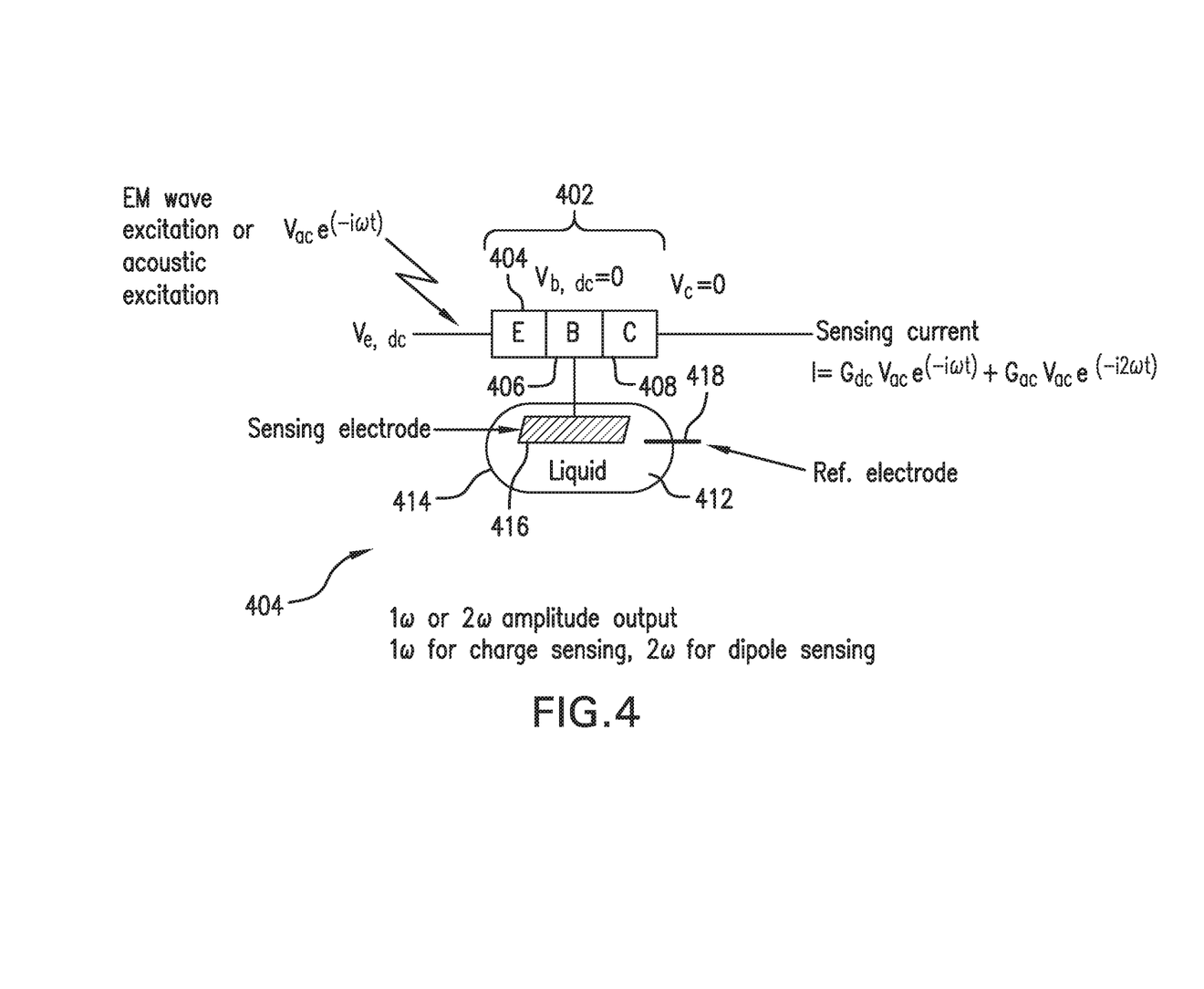
FIG. 4 depicts a sensor employing a BJT with electromagnetic wave excitation and/or acoustic excitation at the emitter, according to an aspect of the invention.

Referring to FIG. 4, an exemplary sensor structure 400 is provided with AC modulation at the emitter E 404. A BJT 402 includes the emitter E 404, a base B 406, and a collector C 408. Note liquid solution 412. The liquid solution 412 is contained in a suitable test vessel 414. The sensing electrode 416 is immersed in the liquid 412 and coupled to the base B 406. Note also the reference electrode 418. A DC input signal $V_{e, dc}$ is applied to the emitter E 404. The base and collector are maintained at ground potential. An AC signal $V_{ac}e^{(-i\omega t)}$ is also applied to the emitter E 404, using electromagnetic wave excitation or acoustic excitation, rather than current modulation as in FIG. 3. The sensing current (i.e. collector current) I is given by equation (2) above. As indicated by the notation "1f or 2f amplitude output," the first frequency component can be taken at the output for charge sensing applications, and the second frequency component for dipole sensing applications. Note that a lock-in amplifier could be connected in FIG. 4 in a similar manner as FIG. 3. Furthermore, alternatives to a lock-in amplifier include a network analyzer, and Fourier analysis.

Furthermore with regard to electromagnetic wave excitation and acoustic excitation, electromagnetic wave excitation can be implemented by using a prism, waveguide, or grating to couple light or other electromagnetic waves to a conductor. Acoustic excitation can be implemented by using a piezoelectric material.

Figure 5:
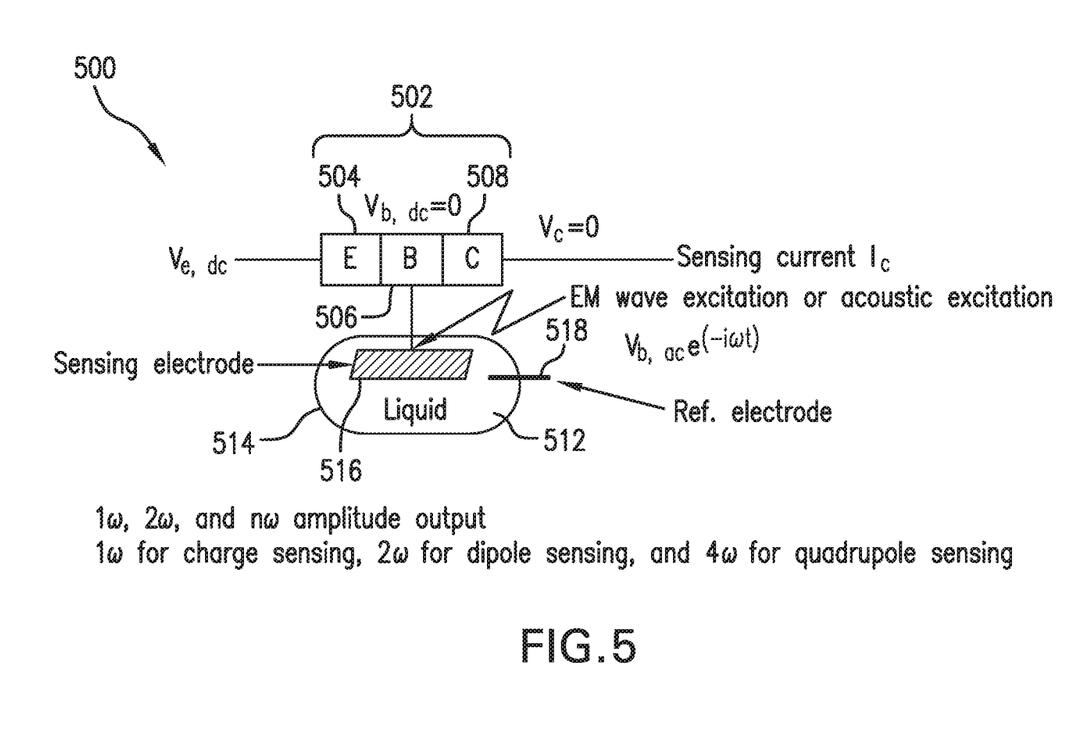
FIG. 5 depicts a sensor employing a BJT with AC modulation at the base, according to an aspect of the invention.

FIG. 5 shows an exemplary sensor structure 500 with AC modulation at the base B 506. A BJT 502 includes an emitter E 504, the base B 506, and a collector C 508. Note liquid solution 512. The liquid solution 512 is contained in a suitable test vessel 514. The sensing electrode 516 is immersed in the liquid 512 and coupled to the base B 506. Note also the reference electrode 518. A DC input signal $V_{e, dc}$ is applied to the emitter E 504. The base B 506 has a DC input voltage of zero. The collector C 508 is maintained at ground potential. An AC signal $V_{b, ac}e^{(-i\omega t)}$ is also applied to the base B 506, using electromagnetic wave excitation or acoustic excitation. The sensing current is the collector current $I_C$. The collector current is proportional to the exponential term of the sensing surface (base) voltage (see Eq. 4), which can be expressed as a sum of harmonic components, $\Sigma I_n e^{in\omega t}$. The base voltage is given generally as:

$$V_b = V_{b,dc} + V_{b,ac} e^{(-i\omega t)} \quad (3)$$

The sensing current is then:

$$I_c = I_0 \exp(q(V_b - \Psi_s - I_b R - V_e)/kT) = \Sigma I_n e^{in\omega t}. \quad (4)$$

Note that:
$\Psi_s$ is the sensing surface potential,
$I_0$ is a constant dependent on device design parameters,
k is the Boltzmann constant,
T is the device temperature in Kelvin, and
q is the electronic charge.
$V_E$ is the voltage applied at the emitter and
$V_B$ is the base voltage applied at base relative to reference electrode
$I_b$ is base current follow through solution
R is resistance of the solution.

As indicated by the notation "$\omega$, $2\omega$ and $n\omega$ amplitude output," the first frequency component can be taken at the output for charge sensing applications, the second frequency component for dipole sensing applications, and the fourth frequency component ($4\omega$) for quadrupole sensing. Again, Fourier transforms can be used to extract multiple harmonic components. Note that a lock-in amplifier could be connected in FIG. 5 in a similar manner as FIG. 3. Furthermore, alternatives to a lock-in amplifier include a network analyzer, and Fourier analysis.

Figure 6:
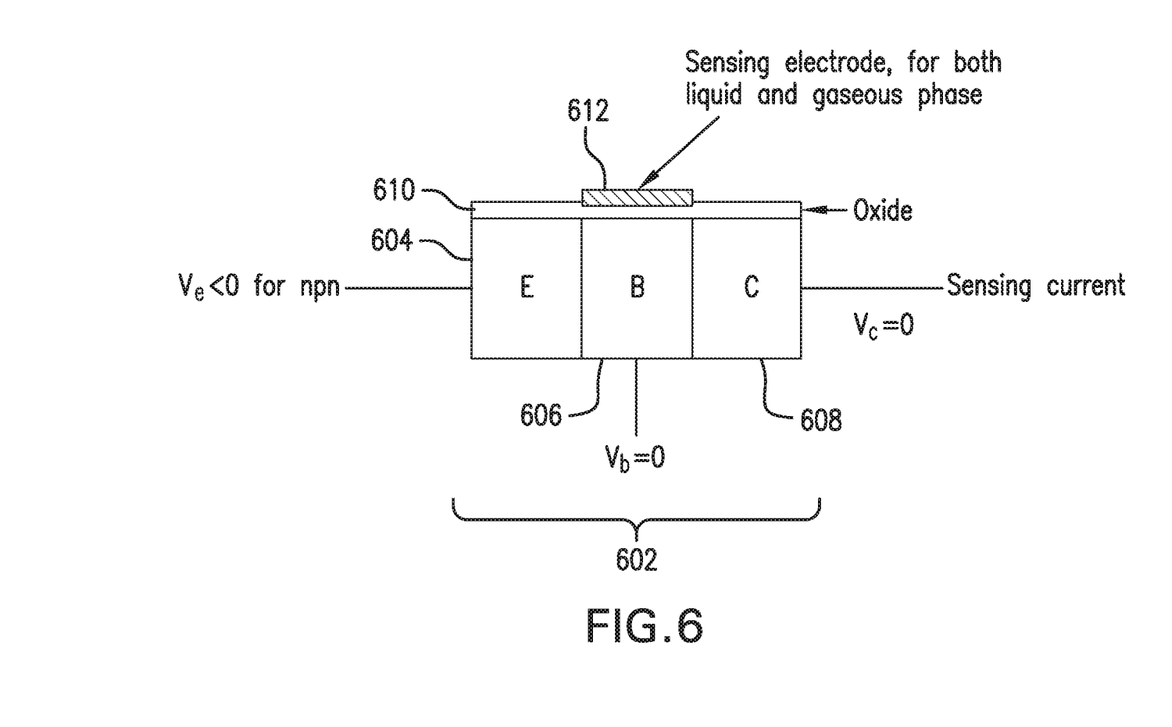
FIG. 6 depicts a BJT with dual base terminal which can be used, e.g., for gas phase sensing, according to an aspect of the invention.

In addition to liquid sensing applications, one or more embodiments can also be used for gas phase sensing. FIG. 6 shows a suitable configuration (for both liquid and gaseous phase). A lateral BJT 602 with a dual base terminal (i.e. two connections to the base) includes an emitter E 604, the base B 606, and a collector C 608, each with a terminal suggested by the wire leads emanating from the bottom. An oxide layer 610 is formed on the top. Sensing electrode 612 on top of oxide 610 is the second terminal of the base 606. Electrode 612 is capacitively coupled to the base. Electrode 612 is in contact with air or another gas or gaseous mixture and detects analytes therein. AC modulation is at the emitter side, in one or more embodiments. Appropriate voltage values for an npn BJT are shown in the figure; the skilled artisan will be able to select appropriate values for pnp configurations.

Figure 7:
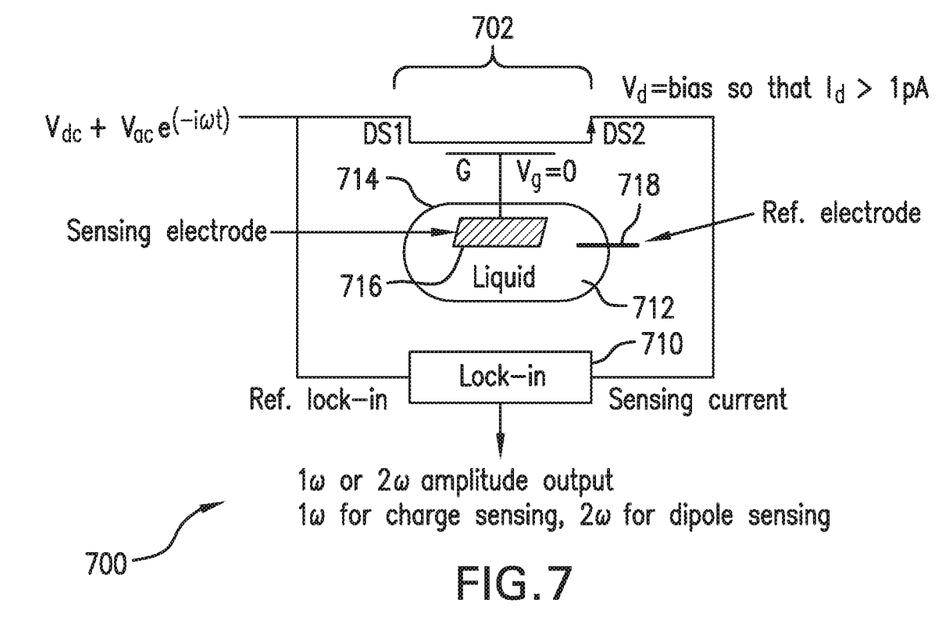
FIG. 7 shows a sensor employing a field effect transistor (FET) with current modulation, according to an aspect of the invention.

FIG. 7 shows an exemplary FET sensor structure 700 with a lock-in amplifier 710 for AC modulation for sensing in solution. A FET 702 includes a first drain-source terminal DS1, a gate G, and a second drain-source terminal DS2. The skilled artisan will appreciate that one of the drain-source terminals functions as a drain and the other as a source depending on the type of transistor and applied voltages. Note liquid solution 712. The liquid solution 712 is contained in a suitable test vessel 714. The sensing electrode 716 is immersed in the liquid 712 and coupled to the gate G. Note also the reference electrode 718. The gate is grounded and the drain-source terminal functioning as the drain is biased to a suitable $V_d$ value; for example, such that the drain current $I_d$ is greater than 1 pico-amp (pA). The current I is given by:

$$I = (G_{dc} + G_{ac} e^{(-i\omega t)})(V_{dc} + V_{ac} e^{(-i\omega t)}) = G_{dc} V_{dc} + G_{dc} V_{ac} e^{(-i\omega t)} + G_{ac} V_{dc} e^{(-i\omega t)} + G_{ac} V_{ac} e^{(-i2\omega t)} \quad (5)$$

The other drain-source terminal has an applied voltage of $V_{dc}+V_{ac}e^{(-i\omega t)}$ and if $V_{dc}=0$, the current I is just:

$$I = G_{dc} V_{ac} e^{(-i\omega t)} + G_{ac} V_{ac} e^{(-i2\omega t)} \quad (6)$$

The input signal $V_{dc}+V_{ac}e^{(-i\omega t)}$ also is coupled to the lock-in amplifier 710 as the reference signal. The sensing current I is the other input to the lock-in amp 710. As indicated by the notation "1f or 2f amplitude output," the first frequency component can be taken at the output for charge sensing applications, and the second frequency component for dipole sensing applications. The skilled artisan will be able to extract the desired frequencies using Fourier analysis or other appropriate techniques.

Figure 8:
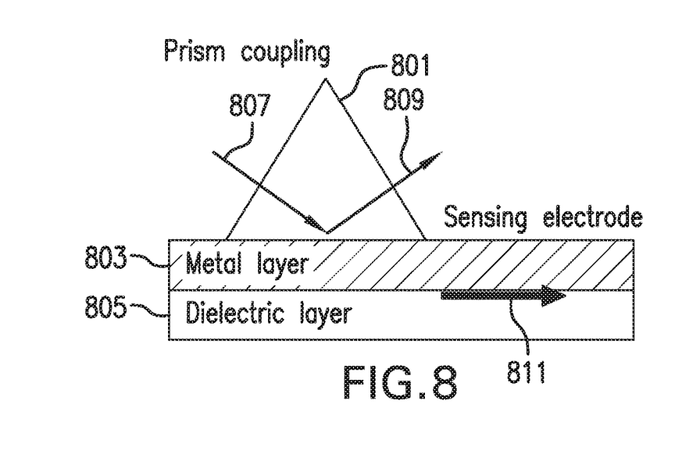
FIG. 8 shows plasma coupling via a prism, according to an aspect of the invention.

FIG. 8 shows plasma coupling via a prism 801, according to an aspect of the invention. In particular, the sensing electrode (which can correspond to any of the depicted embodiments) has a metal layer 803 and a dielectric layer 805; prism 801 couples incident electromagnetic radiation 807 into the electrode with departing radiation shown at 809. Coupled radiation is seen at 811. The exemplary prism in FIG. 8 is triangular.

Figure 9:
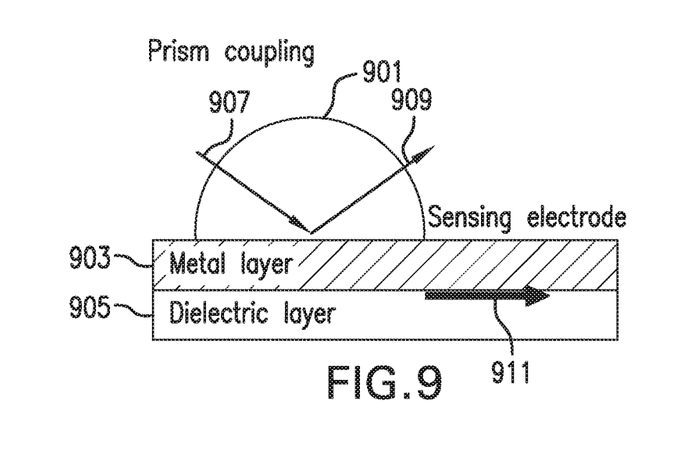
FIG. 9 shows plasma coupling via a different prism, according to another aspect of the invention.

FIG. 9 shows plasma coupling via a "semi-circular prism" 901; elements 901, 903, 905, 907, 909, 911 in FIG. 9 are analogous to elements 801, 803, 805, 807, 809, 811 respectively in FIG. 8. Please note that while a Prism is often thought of as a transparent optical element with flat, polished surfaces that refract light, the circular surface of element 901 can be treated as composition of many small flat facets.

Figure 10:
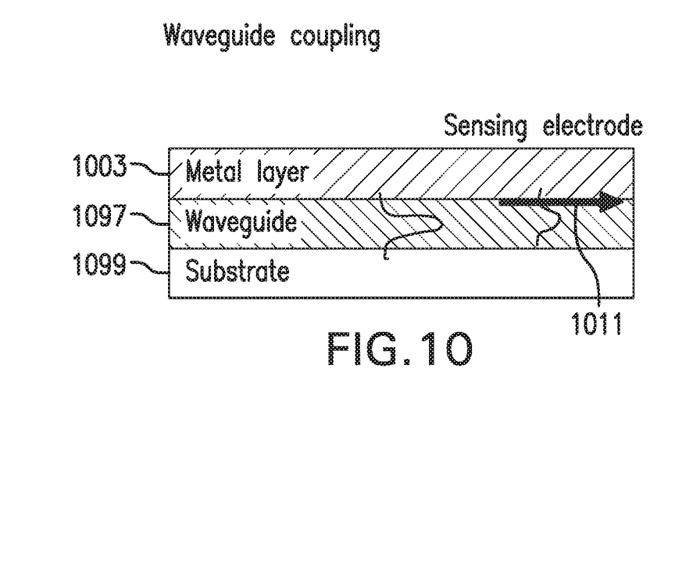
FIG. 10 shows plasma coupling via waveguide coupling, according to an aspect of the invention.

FIG. 10 shows plasma coupling via waveguide coupling, according to an aspect of the invention. In particular, the sensing electrode (which can correspond to any of the depicted embodiments) includes a metal layer 1003 formed outward of a substrate 1099 with an intermediate waveguide 1097 which guides and couples incident electromagnetic radiation into the electrode with coupled radiation shown at 1011.

Figure 11:
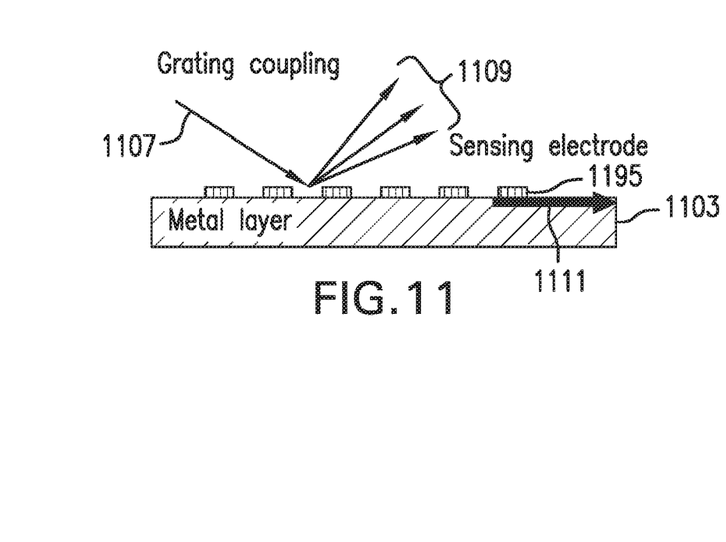
FIG. 11 shows plasma coupling via grating coupling, according to an aspect of the invention.

FIG. 11 shows plasma coupling via grating coupling, according to an aspect of the invention. In particular, the sensing electrode (which can correspond to any of the depicted embodiments) includes a metal layer 1103 which has a grating 1195 thereon; the grating couples incident electromagnetic radiation 1107 into the electrode with departing radiation shown at 1109. Coupled radiation is seen at 1111.

Figure 12:
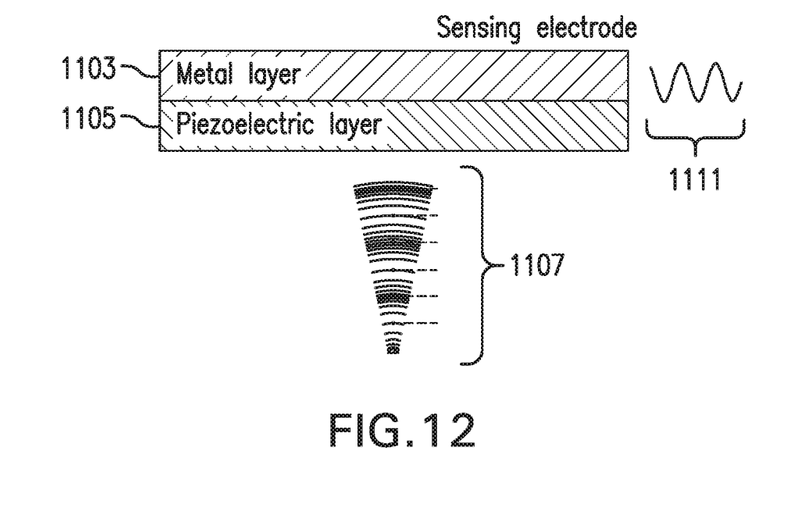
FIG. 12 shows piezoelectric coupling, according to an aspect of the invention.

FIG. 12 shows piezoelectric coupling, according to an aspect of the invention. In particular, the sensing electrode (which can correspond to any of the depicted embodiments) has a metal layer 1103 and a piezoelectric layer 1105; piezoelectric layer 1105 converts incident acoustic radiation 1107 into alternating current 1111.

Suitable materials for sensing electrodes in one or more embodiments include Graphene, Au, Ag, Al, Pt, CNT (carbon nanotubes) and the like. Plasmon coupling can be achieved, for example, via a prism, waveguide, or grating attached to electrodes. Acoustic coupling can be achieved, for example, using piezoelectric material. Sound waves of a suitable frequency are generated and aimed at the piezoelectric material, which then vibrates and generates a time-varying electrical voltage in response. Plasmon and/or acoustic coupling can be applied to the emitter or the base.

One or more embodiments can be employed in a variety of applications; for example, molecular sensing; sensing of proteins; sensing of DNA; sensing in liquid and/or gas and vapor environments. One or more embodiments are not dependent on reduction-oxidation (Redox) reactions. Indeed, one or more embodiments:

work with charge-neutral particles
 are capable of both dipole and charge sensing
 are capable of both liquid and gas phase sensing
 can carry out molecular orientation sensing with dipoles.

One or more embodiments use BJTs for sensing with AC, using either emitter or base modulation.

Some embodiments use electromagnetic wave excitation, such as surface plasmon coupling, with BJTs or FETS.

Some embodiments use acoustic excitation, through piezoelectric coupling, with BJTs or FETS.

Thus, typical prior art transistor-based bio sensor devices measure potential changes due to charges that accumulate to the electrodes. Although the prior art CMOS or FET devices can be very sensitive and fast, the surface electrochemistry of the electrode and the ionic charge interaction limit the speed and sensitivity of the detection. In contrast, in one or more embodiments, a dipole-based detection provided by using an AC field can overcome the slow dynamics associated with charge sensing, improve response time, improve sensitivity, and/or widen the range of detection.

Prior art charge detection-based transistors are limited by the slow dynamics of interface charge trapping and charge transfer and limited type of change detection such as $Cl^-$, pH, etc. AC and dipole-based graphene FETs have limited dynamic range and need calibration.

One or more embodiments employ BJTs with AC excitation to detect dipole oscillation; advantageously providing improved speed, larger dynamic range, higher sensitivity and/or a wider range of detection (such as molecules, DNA, and protein), as compared to prior art methods. One or more embodiments utilize an AC-driven BJT (V+V AC excitation), with integrated lock-in amplification circuitry to pick up the second order current variation.

Given the discussion thus far, it will be appreciated that, in general terms, an exemplary method includes the step of providing a bipolar junction transistor (e.g., 302, 402, 502, 602) having an emitter (e.g. 304, 404, 504, 604), a base (e.g. 306, 406, 506, 606), and a collector (e.g., 308, 408, 508, 608). The base is coupled to a sensing electrode (e.g. 316, 416, 516, 612). A further step includes immersing the sensing electrode in a fluid to be analyzed (e.g., 312, 412, 512, or gas in FIG. 6 not separately numbered). Yet a further step includes biasing the bipolar junction transistor into the active region; for example, applying a direct current voltage ($V_{e,\,dc}$) to the emitter, with the base and the collector being maintained at zero volts DC. In one or more embodiments, the biasing voltage is adjusted such that the collector current (signal) >10 pA and <1 uA.

Still further steps include causing an AC excitation of one of the emitter (FIGS. 3 and 4) and the base (FIG. 5); and carrying out a measurement on a collector current (sensing current) resulting from the AC excitation, to analyze the fluid.

As shown, e.g., in FIGS. 3 and 4, in some cases, the step of causing the AC excitation includes causing the AC excitation to the emitter. The step of causing the AC excitation to the emitter can include, for example, as shown in FIG. 3, applying an AC voltage to the emitter. On the other hand, as shown in FIG. 4, in some cases, the step of causing the AC excitation to the emitter can include surface plasmon coupling electromagnetic waves to the emitter via at least one of a prism, a waveguide, and a grating, or impinging acoustic waves on a piezoelectric material coupled to the emitter. See FIGS. 8-12.

As shown, e.g., in FIG. 5, in some cases, the step of causing the AC excitation includes causing the AC excitation to the base. As shown in FIG. 5, in some cases, the step of causing the AC excitation to the base can include surface plasmon coupling electromagnetic waves to the base via at least one of a prism, a grating, and a waveguide, or impinging acoustic waves on a piezoelectric material coupled to the base.

Referring again to FIG. 3, in one or more embodiments, carrying out the measurement includes providing a lock-in amplifier 310; providing the collector current (sensing current) to a first input of the lock-in amplifier; providing a reference signal to a second input of the lock-in amplifier; and extracting at least one frequency component from an output of the lock-in amplifier, using well-known procedures for the operation of a lock-in amplifier. The extracting can include, for example, implementing charge sensing by extracting a first frequency component; implementing dipole sensing by extracting a second frequency component; and/or implementing quadrupole sensing by extracting a fourth frequency component. Please note that in general, when used in the claims, terms such as "first," "second," "third," "fourth," etc. are used for naming convenience only. However, in the particular case of referring to frequency components, terms such as "first," "second," "third," "fourth," etc. are intended to refer to the specific frequency component mentioned.

The fluid to be analyzed can be, for example, a liquid solution or a gaseous solution. In the latter case, in the providing step, referring to FIG. 6, the emitter, collector, and base have a common upper surface on which is deposited an oxide layer 610. "Upper" is used for convenience as an identifying term and does not necessarily imply that the "upper" surface is in all cases oriented higher than the emitter, collector, and base with respect to the gravity vector. The sensing electrode 612 is formed on an outer surface of the oxide layer 610 and capacitively coupled to said base. In FIG. 6, for example, ground the collector and provide an emitter voltage less than zero to turn the NPN transistor on. Measure the collector current. The skilled artisan knows how to adjust the voltages if a PNP transistor is used instead. In one or more embodiments, the sensing electrode is capacitively coupled in the sense that it acts like a capacitor plate and the oxide acts like the dielectric of a capacitor. Read out can be, for example, via a lock-in amp or network analyzer as described with regard to other embodiments.

In some cases, a further step includes providing a grounded reference electrode 318, 418, 518, 718 in said fluid to be analyzed. The reference electrode is electrically connected to said sensing electrode through said fluid to be analyzed. Reference is made to the aforementioned Sufi Zafar et al. paper "A comparison between bipolar transistor and nanowire field effect transistor biosensors," and specifically to FIG. 1 thereof. In one or more embodiments, the reference electrode is grounded, as is the base, and the reference electrode is connected to the sensing electrode by the solution being analyzed.

In another aspect, another exemplary method, according to another aspect of the invention, includes the step of providing a transistor having at least three terminals. At least one of the three terminals is coupled to a sensing electrode. In the case of a BJT, as seen in FIGS. 3-6, the three terminals include a base, an emitter, and a collector. In the case of a FET, as seen in FIG. 7, the three terminals include a first drain-source DS1, a second drain-source DS2, and a gate G. A further step includes immersing the sensing electrode in a fluid to be analyzed (e.g., 312, 412, 512, 712 or gas in FIG. 6 not separately numbered). A still further step includes biasing the transistor into an operating region suitable for sensing. In the case of a BJT, the transistor can be biased to operate in the active region as described above with regard to FIGS. 3-5. In the case of a FET, the same can be biased, for example, such that the drain current is greater than 100 pA.

Further steps include causing an AC excitation on at least one of the three terminals (e.g., BJT emitter (FIGS. 3 and 4), BJT base (FIG. 5), FET (DS1, DS2, or G)); and carrying out a measurement on a current resulting from the AC excitation, to analyze the fluid. In the case of a BJT, the measurement is carried out on the collector current (sensing current) resulting from the AC excitation, as described above. In the case of a FET, the measurement is carried out on, e.g., the drain current.

The step of causing the AC excitation to the at least one of the three terminals can include surface plasmon coupling electromagnetic waves to the at least one of the three terminals via at least one of a prism, a waveguide, and a grating, and/or impinging acoustic waves on a piezoelectric material coupled to the at least one of the three terminals.

In a further aspect, an exemplary apparatus for analyzing a fluid includes a sensing electrode (e.g. 316, 416, 516, 612). The apparatus also includes a bipolar junction transistor (e.g., 302, 402, 502, 602) having an emitter (e.g. 304, 404, 504, 604), a base (e.g. 306, 406, 506, 606), and a collector (e.g., 308, 408, 508, 608). The base is coupled to the sensing electrode (e.g. 316, 416, 516, 612). Also included is a vessel (e.g. 314, 414, 514) configured to contain the sensing electrode and the fluid to be analyzed (e.g., 312, 412, 512, or gas in FIG. 6 not separately numbered). The apparatus even further includes a biasing circuit (e.g. voltage source which applies DC voltages described with regard to FIGS. 3-5) configured to bias the bipolar junction transistor into the active region, as well as an AC source configured to cause AC excitation of one of the emitter and the base. The apparatus still further includes a measurement circuit (e.g., lock-in amplifier or network analyzer) having a first input coupled to the collector such that a collector current resulting from the AC excitation includes a first input to the measurement circuit; where the measurement circuit is a lock-in amplifier, a second input is provided and configured to receive a reference signal. In any case the measurement circuit has an output from which at least one frequency component can be extracted.

In some instances, such as seen in FIG. 6, the emitter, collector, and base have a common upper surface on which is deposited an oxide layer 610. As noted above, "upper" is used for convenience as an identifying term and does not necessarily imply that the "upper" surface is in all cases oriented higher than the emitter, collector, and base with respect to the gravity vector. The sensing electrode 612 is formed on an outer surface of the oxide layer 610 and capacitively coupled to said base.

Sensors or portions thereof according to one more aspects of the present invention may be realized as integrated circuits; thus, at least a portion of the techniques of one or more aspects or embodiments of the present invention described herein may be implemented in an integrated circuit. In forming integrated circuits, a plurality of identical die is typically fabricated in a repeated pattern on a surface of a semiconductor wafer. Each die can include one or more of the sensors or portions thereof described herein, and may include other structures or circuits, or other types of sensors. The individual die are cut or diced from the wafer, then packaged as an integrated circuit. A person of skill in the art will know how to dice wafers and package die to produce integrated circuits. Integrated circuits so manufactured are considered part of the present invention. Circuits including sensors as described above can be part of the design for an integrated circuit chip. The chip design can be created, for example, in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design can then be converted into an appropriate format such as, for example, Graphic Design System II (GDSII), for the fabrication of photolithographic masks, which typically include multiple copies of the chip design in question that are to be formed on a wafer. The photolithographic masks can be utilized to define areas of the wafer (and/or the layers thereon) to be etched or otherwise processed. Given the teachings herein, the skilled artisan will be able to select known fabrication techniques to produce circuits in accordance with aspects of the invention; e.g., using techniques as disclosed in James D. Plummer et al., Silicon VLSI Technology (2nd Edition), Prentice Hall, 2008.

Resulting integrated circuit chips can be distributed by the fabricator in raw wafer form (that is, as a single wafer that has multiple unpackaged chips), as a bare die or in a packaged form. In the latter case, the chip can be mounted in a single chip package (such as a plastic carrier, with leads that are affixed to a mother board or other higher level carrier) or in a multi-chip package (such as a ceramic carrier that has either or both surface interconnections or buried interconnections). In any case, the chip may then be integrated with other chips, discrete circuit elements and/or other signal processing devices as part of either (a) an intermediate product, such as a mother board, or (b) an end product. The end product can be any appropriate computing product that includes integrated circuit chips.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   providing a bipolar junction transistor having an emitter, a base, and a collector, said base being coupled to a sensing electrode, said emitter, said collector, and said base having a common upper surface on which is deposited an oxide layer, said sensing electrode being formed on an outer surface of said oxide layer and being capacitively coupled to said base;
   immersing said sensing electrode in a fluid to be analyzed, said fluid comprising a gaseous solution;
   biasing said bipolar junction transistor into the active region;
   causing an AC excitation of one of said emitter and said base; and
   carrying out a measurement on a collector current resulting from said AC excitation, to analyze said fluid.

2. The method of claim 1, wherein said step of causing said AC excitation comprises causing said AC excitation to said emitter.

3. The method of claim 2, wherein said step of causing said AC excitation to said emitter comprises applying an AC voltage to said emitter.

4. The method of claim 2, wherein said step of causing said AC excitation to said emitter comprises surface plasmon coupling electromagnetic waves to said emitter via at least one of a prism, a grating, and a waveguide.

5. The method of claim 2, wherein said step of causing said AC excitation to said emitter comprises impinging acoustic waves on a piezoelectric material coupled to said emitter.

6. The method of claim 1, wherein said step of causing said AC excitation comprises causing said AC excitation to said base.

7. The method of claim 6, wherein said step of causing said AC excitation to said base comprises surface plasmon coupling electromagnetic waves to said base via at least one of a prism, a waveguide, and a grating.

8. The method of claim 6, wherein said step of causing said AC excitation to said base comprises impinging acoustic waves on a piezoelectric material coupled to said base.

9. The method of claim 1, wherein carrying out said measurement comprises:
   providing a lock-in amplifier;
   providing said collector current to a first input of said lock-in amplifier;
   providing a reference signal to a second input of said lock-in amplifier; and
   extracting at least one frequency component from an output of said lock-in amplifier.

10. The method of claim 9, wherein said extracting comprises implementing charge sensing by extracting a first frequency component.

11. The method of claim 9, wherein said extracting comprises implementing dipole sensing by extracting a second frequency component.

12. The method of claim 9, wherein said extracting comprises implementing quadrupole sensing by extracting a fourth frequency component.

13. The method of claim 1, further comprising providing a grounded reference electrode in said fluid to be analyzed, wherein said reference electrode is electrically connected to said sensing electrode through said fluid to be analyzed.

* * * * *